US011538453B2

(12) United States Patent
Johnson et al.

(10) Patent No.: US 11,538,453 B2
(45) Date of Patent: Dec. 27, 2022

(54) ULTRASOUND INTERFACE ELEMENT AND METHOD

(71) Applicant: KONINKLIJKE PHILIPS N.V., Eindhoven (NL)

(72) Inventors: Mark Thomas Johnson, Arendonk (BE); Franciscus Johannes Gerardus Hakkens, Eersel (NL); Cornelis Petrus Hendriks, Eindhoven (NL); Daan Anton van den Ende, Breda (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 358 days.

(21) Appl. No.: 16/628,532

(22) PCT Filed: Jun. 28, 2018

(86) PCT No.: PCT/EP2018/067359
§ 371 (c)(1),
(2) Date: Jan. 3, 2020

(87) PCT Pub. No.: WO2019/007787
PCT Pub. Date: Jan. 10, 2019

(65) Prior Publication Data
US 2020/0219480 A1 Jul. 9, 2020

(30) Foreign Application Priority Data
Jul. 4, 2017 (EP) ..................................... 17179486

(51) Int. Cl.
*G10K 11/00* (2006.01)
*G10K 11/18* (2006.01)
*A61B 8/00* (2006.01)

(52) U.S. Cl.
CPC ............ *G10K 11/18* (2013.01); *A61B 8/4281* (2013.01); *A61B 8/4483* (2013.01)

(58) Field of Classification Search
CPC ...... G10K 11/18; A61B 8/4281; A61B 8/4483
See application file for complete search history.

(56) References Cited

U.S. PATENT DOCUMENTS

2006/0030780 A1 2/2006 Gelly et al.
2011/0319768 A1 12/2011 Saito
(Continued)

FOREIGN PATENT DOCUMENTS

CN 1566940 A * 1/2005
CN 1566940 A 1/2005
(Continued)

OTHER PUBLICATIONS

International Search Report for International Application No. PCT/EP2018/067359 filed Jun. 28, 2018, 4 pages.
(Continued)

*Primary Examiner* — Keith M Raymond
*Assistant Examiner* — Adam D. Kolkin

(57) ABSTRACT

An ultrasound interface element (10) is for establishing interface with an incident tissue surface (32) for the purpose of transfer of ultrasound waves. An ultrasound-transmissive active layer (14) is provided comprising one or more responsive material elements (16) deformable in response to an electromagnetic stimulus. The one or more elements are controlled to deform in a manner such as to progressively establish with the tissue surface (32) an outwardly expanding interface, starting from an initial point or line of contact and spreading outwards to a wider area.

20 Claims, 5 Drawing Sheets

(56) References Cited

U.S. PATENT DOCUMENTS

| | | | | |
|---|---|---|---|---|
| 2012/0296214 A1* | 11/2012 | Urabe | ............ | A61B 8/4444 |
| | | | | 600/447 |
| 2013/0015072 A1 | 1/2013 | Hiratsuka et al. | | |
| 2013/0085367 A1* | 4/2013 | Vartak | ............ | A61B 5/6844 |
| | | | | 600/393 |
| 2014/0114193 A1* | 4/2014 | Anthony | ............ | A61B 8/429 |
| | | | | 600/459 |
| 2014/0180134 A1 | 6/2014 | Hoseit | | |

FOREIGN PATENT DOCUMENTS

| | | | |
|---|---|---|---|
| EP | 2514365 A1 | 10/2012 | |
| EP | 2777585 A1 | 9/2014 | |
| JP | S53107190 A | 9/1978 | |
| WO | 2014077931 A2 | 5/2014 | |
| WO | 2016096391 A1 | 6/2016 | |
| WO | 2016180636 A1 | 11/2016 | |
| WO | WO-2016180636 A1 * | 11/2016 | ............ A61B 8/12 |
| WO | 2017036695 A1 | 3/2017 | |

OTHER PUBLICATIONS

Written Opinion of the International Searching Authority for International Application No. PCT/EP2018/067359, filed Jun. 28, 2018, 7 pages.

\* cited by examiner

ULTRASOUND INTERFACE ELEMENT AND METHOD

RELATED APPLICATIONS

This application is the U.S. National Phase application under 35 U.S.C. § 371 of International Application No. PCT/EP2018/067359, filed on Jun. 28, 2018, which claims the benefit of European Application No. 17179486.0, filed Jul. 4, 2017. This application is hereby incorporated by reference herein.

FIELD OF THE INVENTION

This invention relates to an element for facilitating interface between an ultrasound transducer and a receiving surface.

BACKGROUND OF THE INVENTION

In applying ultrasound waves to human or animal tissue, a significant consideration is enabling efficient transfer of the ultrasound vibrations to the tissue. In this regard, ensuring firm contact between ultrasound transducers and the tissue is an important factor so as to avoid loss of efficiency due to air gaps or non-uniform contact.

In current practice, interface between transducers and tissue is facilitated by means of ultrasound-transmissive gel distributed over the incident area of tissue. The gel ensures that no air gaps exist between the transducer and the tissue.

However, use of gel is inconvenient and uncomfortable for patients and inefficient for ultrasound operators, adding extra time and burden to procedures, as well as added cost.

More convenient and efficient means for providing ultrasound interfacing is therefore required.

SUMMARY OF THE INVENTION

The invention is defined by the claims.

According to an aspect of the invention, there is provided an ultrasound interface element, comprising:

an ultrasound-transmissive active layer comprising one or more responsive material elements adapted to deform in response to an electromagnetic stimulus, and the active layer having an upper contact surface adapted for application to an incident tissue surface; and a controller;

wherein the active layer is configurable in a first state in which an initial line or area portion of said upper contact surface of the layer is raised relative to a surrounding area portion, and wherein the controller is adapted to control the one or more responsive material elements to deform out-of-plane of the active layer such as to cause said initial line or area portion to expand smoothly outwards to form a final, larger area portion to thereby establish between the active layer and the incident tissue surface a progressively expanding interface, said control comprising either controlling an array of responsive material elements comprised by the active layer to deform in a sequential pattern outward from said initial line or area portion and across said larger area portion, or controlling a single responsive material element comprised by the active layer extending across at least the entire larger area portion, to transition from an initial convex shape to a second less convex shape.

The invention is based on utilization of responsive materials to establish a secure interface with an incident tissue surface. In particular, the invention provides an interface element having an ultrasound-transmissive active layer which comprises one or more responsive material elements. The responsive material element(s) are controlled to deform in a coordinated way so as to establish a conformal interface with a tissue surface. By conformal interface is meant an interface which conforms to the tissue surface, i.e. morphs to the tissue surface. The element may then provide a deformable acoustic 'window', enabling direct transfer of ultrasound vibrations to the skin, without the occurrence of air gaps.

In use, the ultrasound interface element may be provided coupled to an ultrasound transducer for providing acoustic interfacing with a tissue surface.

As the skilled person will be aware, responsive materials are a class of materials having properties of reversibly deforming or otherwise changing in structural properties in response to one or more electromagnetic stimuli. Varieties of responsive materials include, by way of example, heat-responsive shape-memory materials, such as shape-memory alloys and shape memory polymers, magnetostrictive materials, magnetic shape memory alloys, piezoelectric materials, and photoresponsive materials (photomechanical materials). A further emerging class of materials within the field of responsive materials is that of electroactive materials (EAMs) and electroactive polymers (EAPs) in particular. EAMs can work as sensors or actuators and can be easily manufactured into various shapes allowing easy integration into a large variety of systems. EAMs will be discussed in greater detail below.

Use of responsive materials in connection with ultrasound transducers is not new. However, the use of such materials to enable more efficient acoustic interfacing has not yet been considered. This solution offers a fast, efficient, and reliable way of interfacing transducers with tissue without the need for auxiliary materials such as gels (although embodiments are not incompatible with additional use of gel).

The invention provides a controller adapted to control one or more responsive material elements within an ultrasound-transmissive active layer of the interfacing element to progressively apply the layer onto a tissue surface across an area of desired contact.

For the avoidance of doubt, ultrasound 'transmissive' in the context of the present application means at least partially transmissive (adapted to transmit at least a portion of ultrasound waves which are incident).

In use, a user may make initial provisional application of the active layer of the interface element to the tissue surface, the initial contact typically being imperfect, including air gaps or regions of non-uniform contact. The element(s) are controlled to deform in such a way as to slowly and systematically press and spread the active layer onto and across the tissue surface, starting at an initial small area or line of contact and spreading progressively outward to a final broader area. In consequence of this continuous, progressive application of pressure across the tissue, trapped air pockets or other inconsistencies in surface communication are avoided, and a smooth, conformal interface is established between the active layer and the tissue surface across the whole of the interface area.

The effect of the shape change defined by the invention is that deformation of the active elements is controlled such that an area of the interface between the active layer and an incident tissue surface expands outwardly from an initial sub-region or line of contact to a larger region of contact, such that, at the end of said control, a conformal interface between the active layer and the tissue surface across a continuous region is realised.

There may further be provided one or more ultrasound-transmissive compliant backing layers to which the active layer is coupled. These are preferably arranged to follow the deformation of the active layer. There may be provided for instance a compliant gel cushion layer having an upper surface in communication with the active layer and arranged to follow the deformation of the active layer. This enables efficient acoustic transfer through the two layers and into the tissue surface where, in use, an ultrasound transducer is provided acoustically coupled to an input surface of the compliant gel layer.

The responsive material elements are controlled to deform out of plane in order to establish the progressively expanding interface. By out-of-plane is meant in a direction away from a surface of the active layer. Use of the term is not intended to limit the active layer to a planar layer; the invention is compatible for instance with a curved or contoured layer.

To establish the expanding interface, the active layer is configurable in a first state in which an initial line or area portion of the layer is raised relative to a surrounding area portion, and wherein the controller is adapted to control the one or more responsive material elements to deform out-of-plane such as to cause said first area portion to expand smoothly outwards to form a final, larger area portion.

The necessary progressive, outward application of pressure required to establish the even interface between the active layer and the tissue surface may be achieved in different ways.

It may involve according to a first option controlling an array of responsive material elements comprised by the active layer to deform in a sequential pattern outward from said initial line or area portion and across said larger area portion.

It may involve according to a second option controlling a single responsive material element comprised extending across at least the entire larger area portion, to transition from an initial convex shape to a second less convex shape. The control in this case may comprise transitioning a level of electromagnetic stimulus applied to the single responsive material element to thereby transition the element from said initial convex shape to the second less convex shape.

The single responsive material element may cover the entire larger area portion, i.e. cover the whole surface area of the larger area portion. The single responsive material element may extend across a major portion of the active layer, meaning a majority of the surface area of the active layer. For example, it may cover the majority of the surface area of the active layer. It may extend across, e.g. cover, the whole of the active layer, i.e. the whole of the surface area of the active layer. According to the second option, the active layer may comprise only said single responsive material element and no other responsive material elements.

More particularly, in examples according to the first option, the active layer may comprise a responsive material element which extends across the entirety of the active layer and wherein the controller is adapted to control the element to progressively move from an initial convex shape to a less convex shape, such that when applied to said tissue surface, a conforming interface is established, expanding progressively outward from an apex of said convex shape to a broader region of said less convex shape. The active layer in this case may comprise only this one responsive material element and no others. The responsive material element may cover the entirety of the active layer, i.e. cover the whole surface area of the active layer. The control may comprise transitioning a level of electromagnetic stimulus applied to the responsive material element to thereby transition the element from said initial convex shape to the second less convex shape.

Again, in accordance with this option, the progressively expanding area of interface is realised by gradually transitioning a responsive material element, covering for instance all or substantially all of the area over which contact is desired, from a convex shape to a flat shape. This shape change has the effect of slowly spreading the responsive material element (and active layer) onto the tissue surface starting from an initial middle (apex) area and spreading gradually outward to encompass the entirety (or almost the entirety) of the element (and active layer). The active layer may by way of example comprise a single cohesive layer of responsive material, or may comprise a multi-layer stack of responsive material sub-layers.

More particularly, in examples according to the second option, the active layer may comprise an array of responsive material elements, and wherein the controller is adapted to control the elements of the array to deform in a sequential pattern outwardly from a single element or line of elements within the array, corresponding to said initial line or area portion, such as to progressively establish a conforming interface between the active layer and an incident tissue surface to which the layer is applied, an area of the interface expanding outwardly from said element or line as the responsive material elements are controlled.

Thus, in accordance with this option, the progressively expanding area of interface is realised through coordinated control of an array of responsive material elements, controlled to sequentially actuate in sets, for instance in rows, or lines or annular sets, outward from an initial starting element or line of elements. Activation of the elements may spread outward in all directions or only in one or more directions. In either case, actuation of the elements may continue until all or substantially all have undergone out-of-plane deformation, therefore spreading application of the active layer to the tissue surface across the whole or substantially the whole of its area. Again, due to the progressive outward pressure application, trapped air bubbles or other defects in the interface between the two surfaces is avoided.

By 'array' is meant a regular or non-regular arrangement of responsive material elements distributed across the active layer, separated from one another in directions parallel with a plane or surface profile defined by the layer.

As noted, the controller may be adapted to control the elements to deform in a sequential pattern outwardly in all directions from said single element or line; or the controller may be adapted to control the elements to deform in a sequential pattern outwardly in a subset of one or more directions from said single element or line. This may depend upon where within the array of elements the initial single element or line of elements is located. If it is located centrally, outward sequential deformation in all directions may be most appropriate. Where it is at a location offset from the center, deformation in only a single direction may be more appropriate (e.g. toward the center). As will be discussed below, the location of the initial element or line of elements may be selected based upon a detected initial pressure distribution between the active layer and the tissue surface.

In accordance with any embodiment of the invention, the ultrasound interface element may comprise vibration means for inducing vibration of the active layer. By vibrating the active layer while establishing interface with the tissue surface, air can be driven away from the contact interface, avoiding the trapping of air bubbles which leads to non-ideal surface contact. In addition, vibration can lead to a reduction in friction forces, thereby enabling smooth spreading of the active layer onto the tissue surface without for instance causing folding of skin, which can be another cause of undesired defects in surface interfacing.

Optionally, the vibration means may be provided by one or more of the responsive material elements, the controller being adapted to control the elements to exhibit oscillatory deformation.

Alternatively, a dedicated one or more vibrator elements may be provided to facilitate this effect, or an additional dedicated set of responsive material elements may be provided specifically for the purpose of inducing vibrational effects in the active layer.

In accordance with any embodiment of the invention, the interface element may comprise contact-pressure sensing means for sensing a contact-pressure distribution between the active layer and the tissue surface.

Furthermore, the controller may according to some embodiments then be adapted to: identify, based on said sensed distribution, a line or sub-region of lowest contact pressure between the active layer and the tissue surface; identify a single responsive material element or line of elements spatially aligned with said identified sub-region or line; and select said identified single element or line of elements as the single element or line of elements of said sequential pattern.

The aim of embodiments of the invention is to avoid the occurrence of gaps or breaks in the contact between the active layer and the tissue surface, for instance caused by trapped air pockets or small convex dips in the tissue surface which would typically be 'bridged' over by the active layer rather than filled by the application of the active layer to these regions with sufficient pressure. By identifying a point of lowest initial surface contact-pressure (for instance after initial, light application of the layer to the tissue surface by a user), the above embodiments of the invention effectively identify these regions of greatest perpendicular distance from the tissue surface. By selecting this point or line as the point or line from which progressive out-spreading of the active layer onto the tissue surface is to begin, inadvertent trapping of air pockets within these regions is avoided.

In accordance with one or more examples, the contact pressure sensing means may be provided by one or more of the responsive material elements, the controller bring adapted to sense the contact pressure based on pressure-induced electrical outputs generated by said one or more elements upon an initial manual application of the active layer to the tissue surface. In particular, where the responsive material elements comprise for instance electro-active polymer material (or piezoelectric material), externally induced deformation of the elements (through contact pressure) is converted into electrical outputs having voltage (or current) of a magnitude dependent upon the magnitude of the applied pressure. This way, contact pressure can be measured.

In accordance with one or more examples, contact pressure can be sensed simultaneously with electromagnetically-induced deformation of the elements by applying super-posed low amplitude AC signals and high amplitude DC signals. This will be explained in greater detail in sections to follow.

As an alternative to measuring contact pressure directly, another means for identifying regions of the tissue surface which are indented away from the active layer is to use contact sensing means for identifying regions of contact between the active layer and the tissue surface. The contact sensing means may for instance comprise an array of individually addressable electrodes distributed across an upper surface of the active layer and electrically coupled to the controller.

The controller may be adapted to: detect current flow between any two of the electrodes and use said current flow as indication of contact between said electrodes and the tissue surface. Current flow provides an indication that the area of the active layer carrying the relevant two electrodes has made contact with the tissue surface.

Additionally or alternatively, the controller may be adapted to monitor capacitance between one or more pairs of the electrodes and use changes in said capacitance as indication of contact between said electrodes and the tissue surface.

In either case, the controller may be adapted to select as the point or line from which sequential activation of the elements is to begin, the point of line (or one of the points of lines) at which no such contact is detected.

In accordance with one or more examples, the array of electrodes may be used both for stimulating deformation of the responsive material elements and for sensing contact between the active layer and the tissue surface.

In accordance with any embodiment of the invention, the controller may be adapted, in accordance with one control mode, to control the responsive material elements to deform in directions substantially parallel with the material surface such as to encourage lateral transport of an interfacing fluid or gel disposed between the active layer and the tissue surface. The fluid or gel may for instance be an ultrasound transmissive gel. Small lateral movements of the responsive material elements back and forth (side to side) have been found to push the gel to the outer edges of the contact interface between the active layer and the tissue surface. When the elements are controlled to all deform in the same direction simultaneously, it has been found that the outflow of gel at the leading edge is greater than the inflow at the trailing edge, leading to a net outflow of gel. This can therefore be used when establishing contact to encourage evacuation of gel, to leave as narrow a layer of gel as possible between the active layer and the tissue surface.

In accordance with any embodiment, the one or more responsive material elements may comprise an electroactive material (EAM). This may in particular examples be an electroactive polymer material (EAP). EAPs possess many advantages which may render them superior to other forms of responsive material in embodiments of the invention. These advantages will be discussed in the next section.

In accordance with a further aspect of the invention, there is provided an ultrasound device, comprising: a carrier; one or more ultrasound transducers distributed on the carrier; and an ultrasound interface element as described in any of the embodiments or examples outlined above, or as defined in any of the claims of this application, the interface element arranged in an output path of the one or more ultrasound transducers, for facilitating interface between the transducers and an incident tissue surface to which the ultrasound device is to be applied. The ultrasound transducers are preferably arranged in direct contact with the ultrasound interface element for optimal acoustic coupling of ultrasound waves.

In accordance with a further aspect of the invention, there is provided a method of establishing interface between an ultrasound interface element and an incident tissue surface to which the element is adapted to be applied, the ultrasound interface element comprising an ultrasound transmissive active layer, the active layer comprising one or more responsive material elements adapted to deform in response to an electromagnetic stimulus, and wherein the active layer is configurable in a first state in which an initial line or area portion of said upper contact surface of the layer is raised relative to a surrounding area portion;

and the method comprising:

controlling the one or more elements to deform out-of-plane of the active layer such as to cause said initial line or area portion to expand smoothly outwards to form a final, larger area portion to thereby progressively establish an interface between the active layer and an incident tissue surface, said control comprising either controlling an array of responsive material elements comprised by the active layer to deform in a sequential pattern outward from said initial line or area portion and across said larger area portion, or controlling a single responsive material element comprised by the active layer extending across at least the entire larger area portion, to transition from an initial convex shape to a second less convex shape.

The effect of the shape change defined by the invention is that the deformation is controlled such that an area of the interface expands outwardly from an initial sub-region or line of contact to a larger region of contact, such that, at the end of said control, conformity between the active layer and the tissue across a continuous region is realised.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
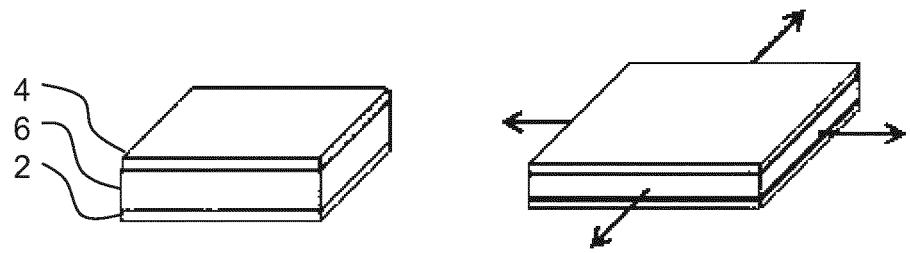
FIGS. 1 and 2 show two possible operating modes for an EAP device.

The invention provides an ultrasound interface element for establishing interface with an incident tissue surface for the purpose of application of ultrasound waves. An ultrasound-transparent active layer is provided comprising one or more responsive material elements deformable in response to an electromagnetic stimulus. The one or more elements are controlled to deform in a manner such as to progressively establish interface between the active layer and the tissue surface, starting from an initial point or line of contact and spreading outwards until a wider area is covered.

In particular, deformation of the one or more elements is such as to cause smooth outward expansion of an initial raised area of the active layer such that when said area is applied against a tissue surface, the expansion is such as to cause establishment of a smooth conformal interface between the active layer and the tissue surface expanding in size with the deformation of the layer.

The invention is based on use of responsive materials to facilitate efficient establishment of an interface.

In preferred embodiments of the invention, the responsive material elements comprise electroactive material (EAM). As noted briefly above, EAMs are a class of materials within the field of electrically responsive materials. When implemented in an actuation device, subjecting an EAM to an electrical drive signal can make them change in size and/or shape. This effect can be used for actuation and sensing purposes. There exist inorganic and organic EAMs. One particular kind of organic EAM is that of electroactive polymers (EAPs).

Electroactive polymers (EAPs) are an emerging class of materials within the field of electrically responsive materials. EAPs can work as sensors or actuators and can easily be manufactured into various shapes allowing easy integration into a large variety of systems. Materials have been developed with characteristics such as actuation stress and strain which have improved significantly over the last ten years. Technology risks have been reduced to acceptable levels for product development so that EAPs are commercially and technically becoming of increasing interest. Advantages of EAPs include low power, small form factor, flexibility, noiseless operation, accuracy, the possibility of high resolution, fast response times, and cyclic actuation.

The improved performance and particular advantages of EAP material give rise to applicability to new applications.

An EAP device can be used in any application in which a small amount of movement of a component or feature is desired, based on electric actuation. Similarly, the technology can be used for sensing small movements.

The use of EAPs enables functions which were not possible before, or offers a big advantage over common sensor/actuator solutions, due to the combination of a relatively large deformation and force in a small volume or thin form factor, compared to common actuators. EAPs also give noiseless operation, accurate electronic control, fast response, and a large range of possible actuation frequencies, such as 0-1 MHz, most typically below 20 kHz.

Devices using electroactive polymers can be subdivided into field-driven and ionic-driven materials.

Examples of field-driven EAPs include Piezoelectric polymers, Electrostrictive polymers (such as PVDF based relaxor polymers) and Dielectric Elastomers. Other examples include Electrostrictive Graft polymers, Electrostrictive paper, Electrets, Electroviscoelastic Elastomers and Liquid Crystal Elastomers.

Examples of ionic-driven EAPs are conjugated/conducting polymers, Ionic Polymer Metal Composites (IPMC) and carbon nanotubes (CNTs). Other examples include ionic polymer gels.

Field-driven EAPs are actuated by an electric field through direct electromechanical coupling. They usually require high fields (volts per meter) but low currents. Polymer layers are usually thin to keep the driving voltage as low as possible. Ionic EAPs are activated by an electrically induced transport of ions and/or solvent. They usually require low voltages but high currents. They require a liquid/gel electrolyte medium (although some material systems can also operate using solid electrolytes).

Both classes of EAP have multiple family members, each having their own advantages and disadvantages.

A first notable subclass of field-driven EAPs are Piezoelectric and Electrostrictive polymers. While the electromechanical performance of traditional piezoelectric polymers is limited, a breakthrough in improving this performance has led to PVDF relaxor polymers, which show spontaneous electric polarization (field-driven alignment). These materials can be pre-strained for improved performance in the strained direction (pre-strain leads to better molecular alignment). Normally, metal electrodes are used since strains usually are in the moderate regime (1-5%). Other types of electrodes (such as conducting polymers, carbon black based oils, gels or elastomers, etc.) can also be used. The electrodes can be continuous, or segmented.

Another subclass of interest of field-driven EAPs is that of Dielectric Elastomers. A thin film of this material may be sandwiched between compliant electrodes, forming a parallel plate capacitor. In the case of dielectric elastomers, the Maxwell stress induced by the applied electric field results in a stress on the film, causing it to contract in thickness and expand in area. Strain performance is typically enlarged by pre-straining the elastomer (requiring a frame to hold the pre-strain). Strains can be considerable (10-300%). This also constrains the type of electrodes that can be used: for low and moderate strains, metal electrodes and conducting polymer electrodes can be considered, for the high-strain regime, carbon black based oils, gels or elastomers are typically used. The electrodes can be continuous, or segmented.

In some cases, thin film electrodes are added when the polymer itself lacks sufficient conductivity (dimension-wise). The electrolyte can be a liquid, a gel or a solid material (i.e. complex of high molecular weight polymers and metal salts). Most common conjugated polymers are polypyrrole (PPy), Polyaniline (PANi) and polythiophene (PTh).

An actuator may also be formed of carbon nanotubes (CNTs), suspended in an electrolyte. The electrolyte forms a double layer with the nanotubes, allowing injection of charges. This double-layer charge injection is considered as the primary mechanism in CNT actuators. The CNT acts as an electrode capacitor with charge injected into the CNT, which is then balanced by an electrical double-layer formed by movement of electrolytes to the CNT surface. Altering the charge on the carbon atoms results in a change of C—C bond length. As a result, expansion and contraction of single CNT can be observed.

Figure 2:
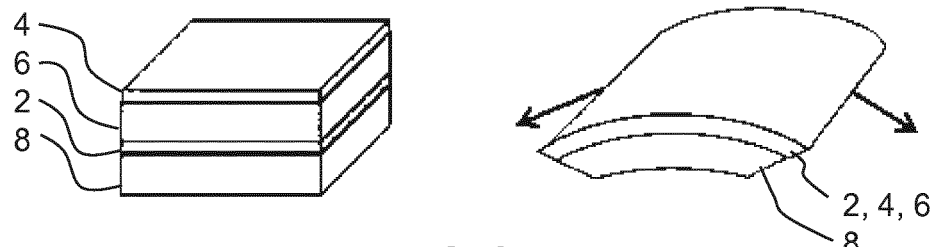

FIGS. 1 and 2 show two possible operating modes for an EAP device.

The device comprises an electroactive polymer layer 6 sandwiched between electrodes 2, 4 on opposite sides of the electroactive polymer layer 6.

FIG. 1 shows a device which is not clamped. A voltage is used to cause the electroactive polymer layer to expand in all directions as shown.

FIG. 2 shows a device which is designed so that the expansion arises only in one direction. The device is supported by a carrier layer 8. A voltage is used to cause the electroactive polymer layer to curve or bow.

Together, the electrodes, electroactive polymer layer, and carrier may be considered to constitute the overall electroactive polymer structure.

The nature of this movement for example arises from the interaction between the active layer, which expands when actuated, and the passive carrier layer. To obtain the asymmetric curving around an axis as shown, molecular orientation (film stretching) may for example be applied, forcing the movement in one direction.

The expansion in one direction may result from the asymmetry in the EAP polymer, or it may result from asymmetry in the properties of the carrier layer, or a combination of both.

An electroactive polymer structure as described above may be used both for actuation and for sensing. The most prominent sensing mechanisms are based on force measurements and strain detection. Dielectric elastomers, for example, can be easily stretched by an external force. By putting a low voltage on the sensor, the strain can be measured as a function of voltage (the voltage is a function of the area).

Another way of sensing with field-driven systems is measuring the capacitance-change directly or measuring changes in electrode resistance as a function of strain.

Piezoelectric and electrostrictive polymer sensors can generate an electric charge in response to applied mechanical stress (given that the amount of crystallinity is high enough to generate a detectable charge). Conjugated polymers can make use of the piezo-ionic effect (mechanical stress leads to exertion of ions). CNTs experience a change of charge on the CNT surface when exposed to stress, which can be measured. It has also been shown that the resistance of CNTs change when in contact with gaseous molecules (e.g. $O_2$, $NO_2$), making CNTs usable as gas detectors.

Simultaneous sensing and actuation can be achieved through superposed application of a low amplitude AC signal (for sensing) with a higher amplitude DC signal (for the primary deformation). The mechanism for achieving this is described in detail for instance in WO 2017/036695.

In the detailed examples which follow, responsive material elements comprising EAP material are provided. However, this is by way of illustration only, and in all cases it is to be understood that in the embodiments described, the EAP material element may be replaced by a different variety of responsive material element (stimulated by a suitable stimulus) without altering the general concept, functioning or achieved general advantages of the invention.

Figure 3:
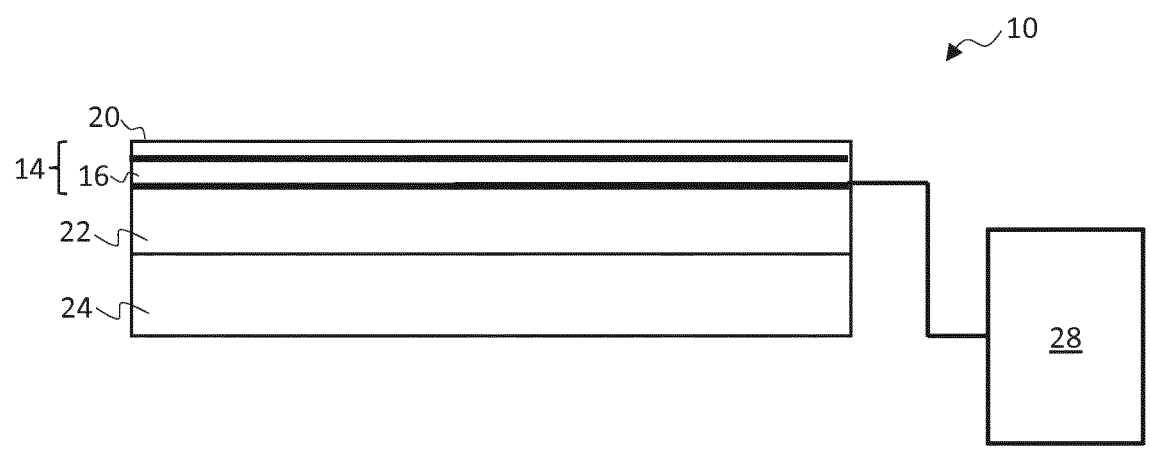
FIG. 3 shows an example ultrasound interface element in accordance with one or more embodiments of the invention.

FIG. 3 shows a schematic illustration of one example ultrasound interface element 10 in accordance with one or more embodiments of the invention. The interface element is for installation over an ultrasound transducer or transducer array for facilitating efficient out-coupling of ultrasound waves into a receiving medium. The interface element comprises an ultrasound transmissive active layer 14 comprising one or more responsive material elements. By way of example, in the particular interface element illustrated in FIG. 3, the active layer comprises a multi-layer stack comprising a first responsive material element 20 (e.g., a first silicone layer) and a second responsive material element 16 (e.g., a second PVDF-TrFE layer). In this example, the silicone layer and PVDF-TrFE layer provide deformable responsive material elements. A greater number of layers may be provided included in further examples. However two are shown in FIG. 3 for illustration.

Stacked beneath the active layer is a backing layer 22 for facilitating out-of-plane bending of the active layer upon deformation. Stacked beneath the backing layer is a compliant cushion layer 24. The compliant cushion layer preferably comprises an encapsulated volume of ultrasound transmissive gel.

The backing layer 22 may be selected or configured such as to have an acoustic impedance which matches that of the ultrasound transmissive active layer 14 so as to avoid internal acoustic reflections at the interface between these two layers.

Although a compliant cushion layer 24 is provided in the present example, this is not essential to the present invention and may be omitted.

The one or more responsive material elements 16, 20 of the ultrasound transmissive active layer 14 are provided one or more respective pairs of electrodes (not shown in FIG. 3) for applying electromagnetic stimuli for stimulating deformation of the responsive material elements. The electrodes are operatively coupled to a controller 28 which is adapted to control application of stimuli to the electrodes such as to induce desired patterns of deformation of the ultrasound transmissive active layer 14. The electrodes are preferably ultrasound transmissive.

The material layer(s) 16, 20 of the active layer structure may (each) comprise a single layer of responsive material, or may comprise an array of responsive material elements. As noted, there may be provided a multi-layer stack of responsive material elements, where these optionally may be formed of different materials.

Although a compliant cushion layer 24 is provided in the present example, this is not essential. Preferably the cushion layer comprises an encapsulated volume of deformable material, where this may be an oil, liquid, deformable polymer material, or, most preferably, a gel. The cushion layer may provide improved acoustic interfacing between an ultrasound transducer and the ultrasound transmissive active layer 14. This is because a lower surface of the cushion layer may deform in a different shape to an upper surface, allowing the upper surface to follow the deformation of the active layer, while the lower surface by contrast may bend and conform to an output surface of an ultrasound transducer which is applied to it. Thus, efficient coupling between the two may be enabled.

The compliant cushion layer may by way of example comprise an encapsulated volume of gel. This may include, by way of non-limiting example a hydrogel, uncured polybutadiene rubber or other visco/elastic material.

In contrast to some prior art devices, in accordance with the present invention, the responsive material elements of the ultrasound transmissive active layer 14 are arranged such that, in use, they lie within the acoustic path of ultrasound waves being transmitted through the ultrasound interface element 10. Accordingly, it is necessary that the ultrasound transmissive active layer 14 be ultrasound transmissive. To this end, electrodes driving the responsive material element may be provided which are acoustically transparent (or at least partially transparent or transmissive). The electrodes may for instance be sub-micron metal layers or conductive polymers. Alternatively, the electrodes may comprise of certain carbon-like materials, such as for instance graphene, carbon black, or carbon nanotubes.

For the purposes of the present example, it will be assumed that the ultrasound interface element 10 comprises responsive material elements 16, 20 comprising electroactive polymer material. However, this is for illustration only, and other responsive materials are compatible with the embodiments.

In use, the one or more EAP elements 16, 20 of the ultrasound transmissive active layer 14 are controlled to deform such as to cause out-of-plane deformation or expansion or the ultrasound transmissive active layer 14. When the ultrasound interface element 10 is arranged in proximity to, or held provisionally against, an incident tissue surface, the deformation establishes interface between an upper surface of the ultrasound transmissive active layer 14 and the incident tissue surface.

Figure 4:
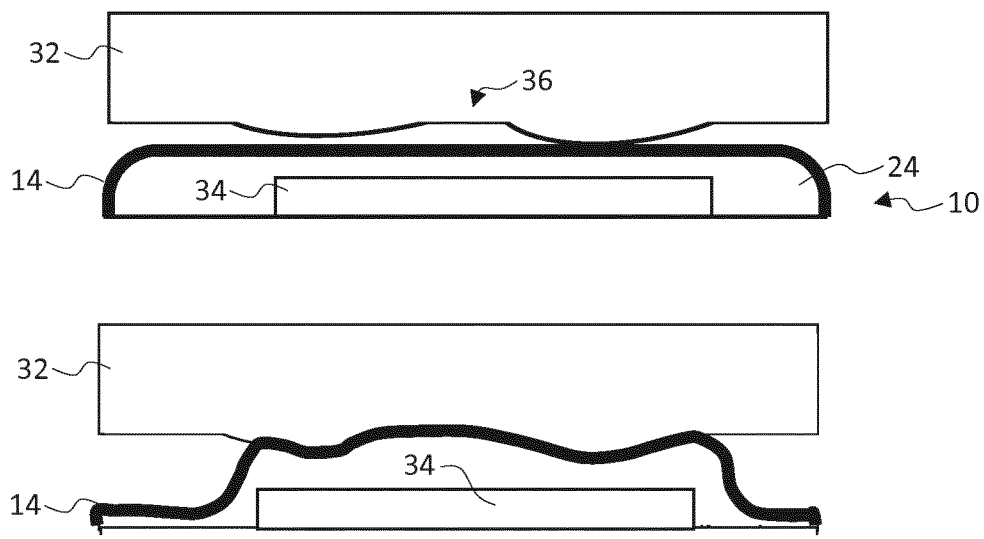
FIG. 4 illustrates a first control approach for an ultrasound transmissive layer not according to the invention.

This is illustrated schematically in FIG. 4 which shows the ultrasound interface element 10 arranged over an ultrasound transducer 34. The upper image of FIG. 4 shows the ultrasound interface element 10 applied provisionally against a layer of tissue 32 having a non-even tissue surface. Stimulation of the responsive material elements of the ultrasound transmissive active layer 14 and consequent deformation of the active layer causes establishment of contact between the active layer and the surface of tissue 32 (as shown in the bottom image of FIG. 4). Optionally, the responsive material layer(s) of the ultrasound transmissive active layer 14 may be clamped at the sides, enabling generation of larger forces.

However, in practice, mere uniform stimulation of EAP elements 16 of the ultrasound transmissive active layer 14 may not result in the ideal conformity between the two contacting surfaces illustrated in FIG. 4. In particular, it may be difficult to obtain good contact within the region around the illustrated dip 36 in the tissue positioned close to the center of the ultrasound transmissive active layer 14 since air may become trapped as contact is established, or skin around the dip may fold. In other regions also, skin folding may be an issue when the ultrasound transmissive active layer 14 is simply applied flatly onto the surface of tissue 32. Skin folding impedes ideal contact between the two surfaces.

In embodiments according to the invention therefore, deformation of the ultrasound transmissive active layer 14 is performed non-uniformly, beginning only with one small protruding area and smoothly expanding this area outwards until a broader area of interface is established. By controlling gradual outward expansion of an area of interface, trapped air pockets caused by concave regions are avoided, and folding of skin can be prevented.

Two main approaches are possible: establishing an expanding interface using a single deforming EAP element, and establishing an expanding interface using coordinated deformation of an array of EAP elements. Embodiments making use of an array of EAP elements will first be described.

Figure 5:
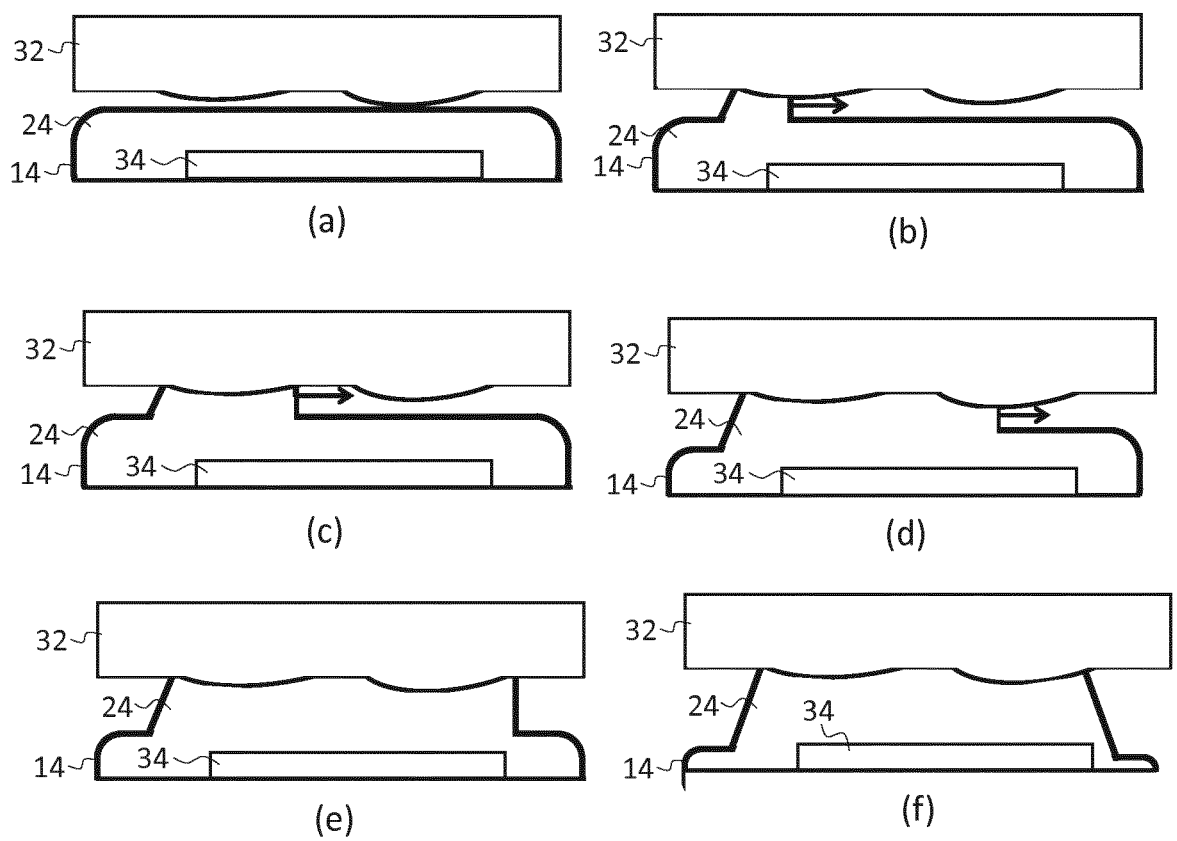
FIG. 5 illustrates a first mode of control of an ultrasound transmissive layer in accordance with one or more embodiments of the invention.

A first example is illustrated in FIG. 5. In accordance with this embodiment, interface between the ultrasound transmissive active layer 14 and the surface of tissue 32 is expanded outwards from a single initial point (sub-region) of contact.

An ultrasound interface element 10 comprises an ultrasound transmissive active layer 14 comprising an array of EAP elements, controllable to deform out-of-plane of the ultrasound transmissive active layer 14 in response to application of respective electrical stimuli using provided electrodes (not shown). The interface element is shown arranged over an ultrasound transducer 34, and applied provisionally to a surface of tissue 32 (FIG. 5(a)). Controlled deformation of the EAP elements is shown in FIGS. 5(b)-(f).

A first, initial area of interface is established (FIG. 5 (b)) by controlling out of plane deformation of a small subset of EAP elements localized within a single small sub-region of the ultrasound transmissive active layer 14. This causes formation of a small protrusion from the surface of the ultrasound transmissive active layer 14 which is pressed by the force of the EAP deformation onto surface of tissue 32.

This small initial area of interface is then smoothly expanded outward to cover a progressively larger and larger area of interface between the two surfaces. This is achieved as shown in FIGS. 5 (*c*)-(*f*) by actuating EAP elements of the array sequentially outward from the initially actuated subset such that an ever wider area of out-of-plane deformation ealizedsed. This causes progressive expansion of an area of interface between the ultrasound transmissive active layer 14 and the tissue surface until a broad area of interface has been realised. Due to the smooth expansion of the interface outwards, trapping of air in any concavities is avoided.

FIG. 5 shows a sectional view, where, for illustration, expansion of the interface along a single direction (toward the right) is shown. However, expansion of the interface in two dimensions may in practice be effected, through controlled outward deformation in both X and Y dimensions.

Alternatively to controlling expansion of an interface from a single point or sub-region, expansion from a single initial line of contact may be realised. Here, initial contact between the ultrasound transmissive active layer 14 and the surface of tissue 32 is realised by out-of-plane deformation of an initial line of EAP elements of the array. Following this, neighboring EAP elements are sequentially actuated, expanding the interface linearly over the complete surface of tissue 32. Again, this mode of establishing interface reduces the risk of trapping of air pockets or folding of skin.

While controlling deformation of the EAP elements of the ultrasound transmissive active layer 14 to establish the interface, contact pressure between the layer 14 and the surface of tissue 32 may be monitored. This may be achieved through the method described in WO 2017/036695, wherein simultaneous actuation and sensing using EAP elements can be achieved through superposed application of AC and DC signals to the elements.

By monitoring contact pressure as deformation is controlled, the deformation pressure can optionally be adjusted in real time so as to ensure a tight interface is maintained between the ultrasound transmissive active layer 14 and the surface of tissue 32 at all times. A feedback system is thereby established. The pressure can be altered by controlling the strength of the applied stimulus to thereby subtly adjust the extent of deformation. The deformation pressure may be adjusted to as to ensure uniform application of pressure across the entire interface area.

By using the described approach to establish interface between the ultrasound interface element 10 and the surface of tissue 32, the quantity of interfacing gel and the required contact pressure (to ensure conformity between the two surfaces) may be reduced.

In accordance with any embodiment of the invention, means may be provided for effecting vibration of the ultrasound transmissive active layer 14. By vibrating the active layer while establishing an interface, air which might otherwise become trapped may be driven away or dispersed from the contact interface. The use of vibration may be combined with any of the interface-establishing approaches described in the present disclosure.

In addition to dispersing air, vibration may also induce a reduction in frictional force between the ultrasound transmissive active layer 14 and the surface of tissue 32. This hence enhances smooth coverage of the surface without for example inducing folding of skin.

The vibration means may be provided by the EAP elements of the array themselves. This may be realised for instance though application of high frequency signals superposed atop the main DC deformation signal, causing oscillatory deformation (as described for instance in WO 2017/036695). Alternatively, separate vibration means may be provided in the form of a dedicated vibrator, mechanically coupled to the active layer.

For most effective establishment of an interface, ideally, the outward spreading of the interface area described above should begin at a point of lowest initial contact pressure between the ultrasound transmissive active layer 14 and the surface of tissue 32. The reason for this is that the points of lowest initial contact pressure correspond to the areas of the tissue in which air is most likely to become trapped, or skin is most likely to become folded. In the example of FIG. 4 for instance, the area of lowest initial contact pressure would be dip 36, this point being the most perpendicularly displaced relative to the ultrasound transmissive active layer 14.

In accordance with a subset of embodiments therefore, the controller may be adapted to sense, using the array of EAP elements, an initial distribution of contact pressure between the ultrasound transmissive layer and the surface of tissue 32 and, based on this, to identify a sub-region or line of lowest contact pressure. This line or sub-region is then selected as the line or sub-region from which expansion of the interface is controlled, in the manner for instance illustrated in FIG. 5.

Figure 6:
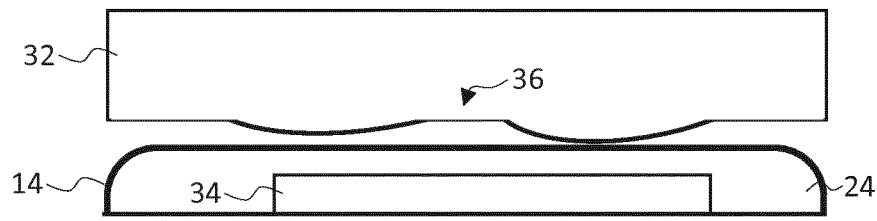
FIG. 6 illustrates a further mode of control of an ultrasound transmissive layer in accordance with one or more embodiments of the invention.
Figure 6:
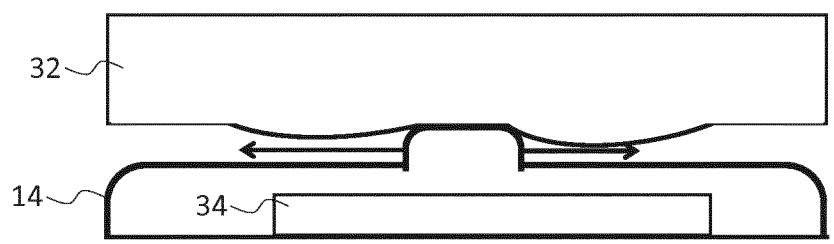

FIG. 6 schematically illustrates this approach.

To measure the pressure distribution, the controller 28 may be adapted to control the EAP elements 16 of the ultrasound transmissive active layer 14 to first deform uniformly, such that the whole of the layer 14 is applied evenly to the surface of tissue 32 with an initial contact force. This is shown on the left of FIG. 6. The controller may then measure a distribution of contact pressure across the ultrasound transmissive active layer being applied to the EAP elements by the tissue surface. This may be ascertained simultaneously to the uniform actuation of the layer by means of the method described for instance in WO 2017/036695.

The point to make first contact as the EAP elements are uniformly activated will typically be the point of lowest contact pressure.

Once the point, sub-region or line or lowest contact pressure has been identified, the EAP elements may be retracted, and establishment of conformal interface performed through outward expansion of an initial area of interface, beginning from an initial contact area or line established at said identified point, sub-region or line of lowest contact pressure. This is shown on the right of FIG. 6. Here, the central dip 36 is identified as the sub-region of lowest pressure, and the controller controls deformation of the ultrasound transmissive layer outward from this sub-region.

Alternatively to measuring pressure distribution, regions of the surface of tissue 32 being most indented (or normally displaced relative to a surface of the ultrasound transmissive layer) may be identified through direct contact detection. Here, the EAP elements are controlled to deform uniformly as in the example above, but in preference to measuring pressure, a set of electrodes is used to detect points of contact between the ultrasound transmissive active layer 14 and the tissue surface. In this way, points of non-contact may be identified and ascribed as likely regions of indentation. This method may be more sensitive than a pressure-sensing method, and can detect contact at very low initial contact pressures.

Points of contact between the ultrasound transmissive active layer 14 and the surface of tissue 32 may be measured electrically (e.g. resistively or capacitively). This may be facilitated by means of an array of electrodes disposed across a top surface of the ultrasound transmissive active layer 14.

Figure 7:
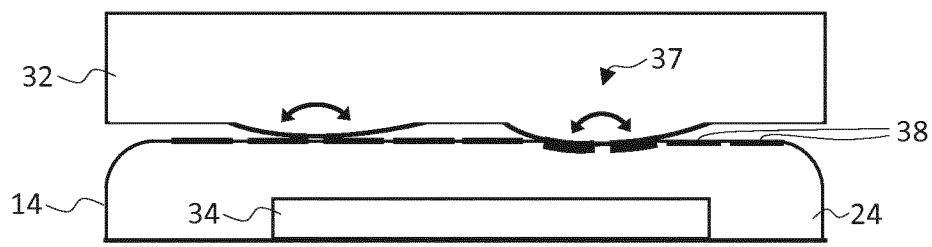
FIG. 7 illustrates a further mode of control of an ultrasound transmissive layer based on contact pressure sensing in accordance with one or more embodiments of the invention.
Figure 7:
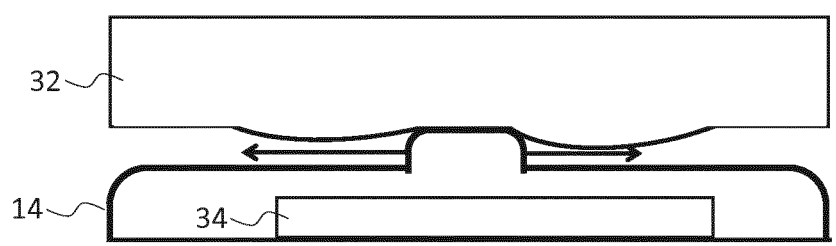

An example of resistive contact sensing is illustrated schematically in FIG. 7 which shows an ultrasound interface element 10 arranged over an ultrasound transducer 34. Across a top surface of the ultrasound transmissive active layer 14 is arranged an array of electrodes 38 operatively coupled to the controller 28 (not shown). Preferably the electrodes 38 are the same electrodes as used for stimulating the array of EAP elements comprised by the ultrasound transmissive active layer 14. This avoids providing a separate, passive layer of electrodes overlaid the active layer, which may hamper the deformation action.

Preferably, each of the electrodes 38 is individually connected to the controller to enable each to be separately addressed for sensing. Preferably, the electrodes are also interconnected with one another to enable, for actuation, all electrodes to be easily activated together (where uniform stimulation is to be performed).

To identify indented regions, the EAP elements are first controlled to deform uniformly such that an initial, provisional contact is established, as shown in FIG. 7 (upper image).

Points or regions of contact between the ultrasound transmissive active layer 14 and the surface of tissue 32 may be detected by monitoring for current running between any two adjacent electrodes 38. This is illustrated in FIG. 7 (top), where contact between the protrusion 37 on the right of the surface of tissue 32 and the ultrasound transmissive active layer 14 is detectable through current running through the two electrodes making direct contact with it (shown in bold).

The uniform deformation may be continued so as to detect further points which come into contact. By continuing this process, points of indentation can be identified as those which do not make contact with the ultrasound transmissive active layer 14 or which make contact last. These may be selected as the points or sub-regions from which an interface between the ultrasound transmissive active layer 14 and surface of tissue 32 is expanded outward.

This is shown at the bottom of FIG. 7. The middle dip 36 is identified as the point of greatest indentation. The controller controls expansion of interface outward from this region to peripheral regions. By spreading the interface area outward from the point of greatest indentation, any potential trapped air in this region is avoided.

Figure 8:
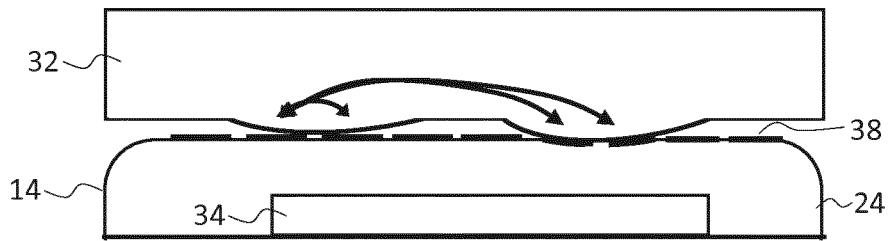
FIG. 8 illustrates a further mode of control of an ultrasound transmissive layer based on contact detection in accordance with one or more embodiments of the invention.
Figure 8:
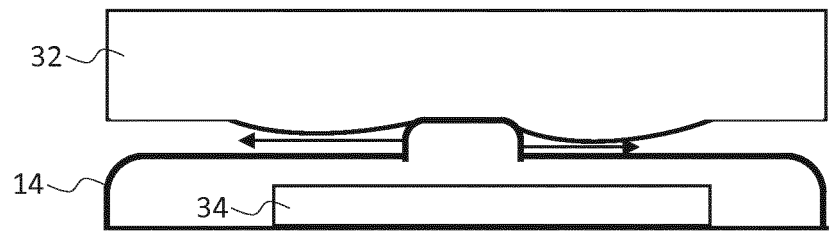

Alternatively to resistive sensing, contact may also be sensed capacitively in accordance with further examples. An example is illustrated schematically in FIG. 8.

Again, the ultrasound transmissive active layer 14 is provided with an array of electrodes 38 across its top surface. Preferably, these are the same electrodes as used for stimulating the EAP elements of the layer so as to minimize the number of required parts for the ultrasound interface element 10. The electrodes are preferably individually addressable for sensing.

The electrodes 38 may be operated as (planar) capacitive sensors, wherein a capacitive difference between one set of electrodes and a selected reference may be detected and used to indicate contact between said pair of electrodes and surface of tissue 32.

The above described embodiments utilize an array of electrodes to deform an ultrasound-transmissive layer in a manner such as to establish an outwardly expanding interface area. In accordance with a second approach, a single layer of EAP material may be provided, adapted to deform in response to a suitable electrical stimulus such as to establish an interface expanding outwardly from an initial point of contact.

Figure 9:
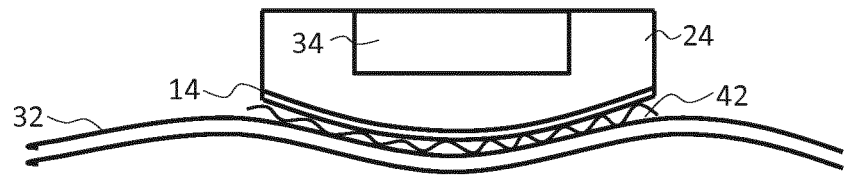
FIG. 9 illustrates a further mode of control of an ultrasound transmissive layer based on use of a single layer of EAP.
Figure 9:
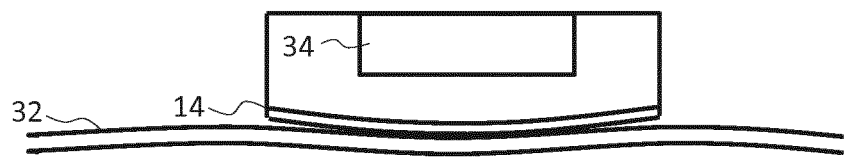

An example is illustrated schematically in FIG. 9. In accordance with this example, an ultrasound interface element 10 is provided comprising an ultrasound transmissive active layer 14, arranged covering a compliant cushion layer 24, which may be a compliant gel. The interface element is arranged over an ultrasound transducer 34. The ultrasound transmissive active layer 14 comprises a single layer of EAP which is controllable by stimulation to deform from a first convex shape (FIG. 9, top) to a second (substantially) flat shape (FIG. 9, bottom).

When held, as shown in FIG. 9, against an incident surface of tissue 32, this deformation causes a gradual outwardly expanding application of pressure across the tissue surface, which leads to establishment of a smooth, conformal interface (i.e. the ultrasound transmissive active layer 14 and surface of tissue 32 are pressed in conformity against one another). The convex to flat deformation achieves effectively the same effect as the embodiments of FIGS. 3-8, in that an initial sub-region of contact is established (in this case, the region covered by the apex of the convex shape), and surrounding neighboring regions of the layer are then drawn up to the level of the sub-region, so as to progressively expand the area of contact. In this way, a smooth out-spreading of the layer 14 across the tissue surface is achieved.

As illustrated in FIG. 9, this single EAP layer embodiment also confers the advantage of enabling efficient evacuation of interfacing gel 42 from between the active layer and the surface of tissue 32.

In general, squeezing out a gel from between a flat layer and a soft substrate is difficult due to the pressure distribution, which typically has a maximum in the outer region of contact, and a minimum somewhere near the middle. As a result the net gel flow is typically directed towards the center of the area of interface. In order to achieve a net outflow across the whole contact area (i.e. transport toward the edges), the pressure must continuously decrease from a maximum in the middle, to zero or minimum at the edge. This can be achieved with the single EAP element actuator of the present embodiment, which initially has macroscopic convex shape (pre-curved or via actuation), and which slowly adapts a flat shape.

In accordance with a further variation, a net outflow of gel from between an embodiment of the interface element and a tissue surface can also be achieved via small lateral (reciprocating) movements (i.e. back and forth). In each lateral movement, the outflow at the trailing edge is greater than the inflow at the leading edge, leading to a net outflow. By means of an array of EAP elements, or a suitably adapted EAP layer, such alternating lateral movements may be effected in accordance with a dedicated control mode so as to drive evacuation of gel from between the element and the tissue surface.

Evacuation of gel from between the interface element and the tissue surface may be useful to provide the closest contact between the two surfaces possible for best acoustic interfacing.

In accordance with an aspect of the invention, there is also provided an ultrasound device for administering ultrasound to a subject, the device comprising an ultrasound interface element in accordance with any embodiment of the invention. The structure of device may be substantially as illustrated in each of FIGS. 4-9, wherein an ultrasound transducer 34 is provided having an ultrasound interface element 10 according to the invention overlaid above it. Preferably, as in each of the examples of FIG. 4-9, there may be a layer of the compliant cushion layer 24 between the ultrasound transducer and the ultrasound transmissive active layer 14 to facilitate good acoustic interfacing between these two components.

An ultrasound imaging device according to an embodiment of the invention may be provided as part of an ultrasound probe or an ultrasound patch (suitable for long term monitoring), such as a surface probe or as part of an endo cavity probe. The device may also be used for transesophageal echo (TEE) and endo bronchial ultrasound.

In another embodiment such an ultrasound interface element forms a part of an ultrasound based monitoring patch arranged to monitor a variation of hemodynamic parameters such as blood flow over an extended period of time. This gives a benefit of assuring that the patch is acoustically coupled to the skin throughout the period of monitoring time without user's interference. The conformity of the ultrasound interface element with the incident tissue (skin) surface allows avoiding developing air bubbles at the interface, thereby assuring an improved quality of the measured signal.

There may further be provided an imaging controller operatively coupled to the ultrasound transducer 34 for processing ultrasound echoes received at the transducer to generate ultrasound images.

An ultrasound imaging or monitoring device according to an embodiment of the present invention may form part of or be provided as part of a wider ultrasound diagnostic imaging or monitoring system.

Figure 10:
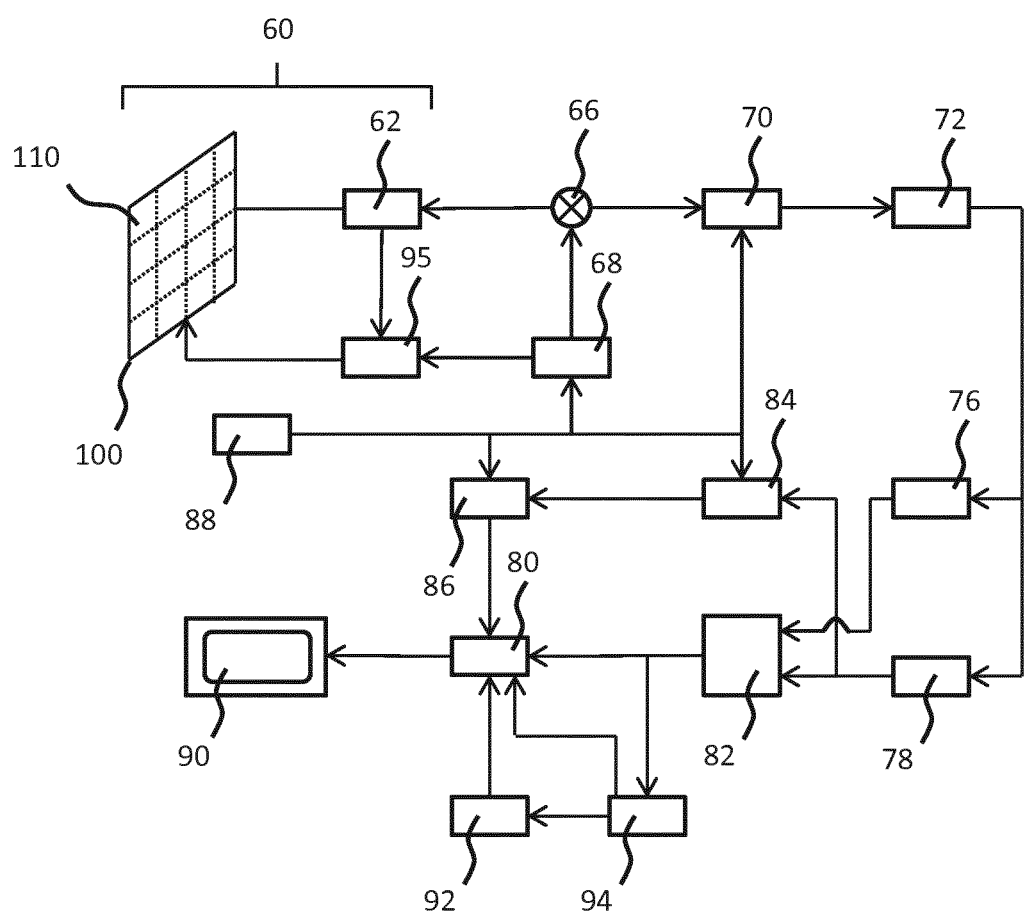
FIG. 10 shows a block diagram of an exemplary ultrasound diagnostic imaging system.

The general operation of an exemplary ultrasound system will now be described, with reference to FIG. 10.

The exemplary system comprises an array transducer probe 60 which has a CMUT transducer array 100 for transmitting ultrasound waves and receiving echo information. The CMUT transducer array 100 may alternatively comprise piezoelectric transducers formed of materials such as PZT or PVDF. The transducer array 100 is a two-dimensional array of transducers 110 capable of scanning in a 2D plane or in three dimensions for 3D imaging. In another example, the transducer array may be a 1D array.

The CMUT transducer array 100 is coupled to a microbeamformer 62 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 62 is coupled by the probe cable to a transmit/receive (T/R) switch 66 which switches between transmission and reception and protects the main beamformer 70 from high energy transmit signals when a microbeamformer is not used and the transducer array is operated directly by the main system beamformer. The transmission of ultrasound beams from the array transducer probe 60 is directed by a transducer controller 68 coupled to the microbeamformer by the T/R switch 66 and a main transmission beamformer (not shown), which receives input from the user's operation of the user interface or control panel 88.

One of the functions controlled by the transducer controller 68 is the direction in which beams are steered and focused. Beams may be steered straight ahead from (orthogonal to) the transducer array, or at different angles for a wider field of view. The transducer controller 68 can be coupled to control a DC bias control 95 for the CMUT array. The DC bias control 95 sets DC bias voltage(s) that are applied to the CMUT cells.

In the reception channel, partially beamformed signals are produced by the microbeamformer 62 and are coupled to a main receive beamformer 70 where the partially beamformed signals from individual patches of transducers are combined into a fully beamformed signal. For example, the main beamformer 70 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processor 72. The signal processor 72 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed to take into account the characteristics of the transmission beamformer. In FIG. 10 only the receiver beamformers 62, 70 are shown, for simplicity. In the complete system, there will also be a transmission chain with a transmission micro beamformer, and a main transmission beamformer.

The function of the microbeamformer 62 is to provide an initial combination of signals in order to decrease the number of analog signal paths. This is typically performed in the analog domain.

The final beamforming is done in the main beamformer 70 and is typically after digitization.

The transmission and reception channels use the same transducer array 60' which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 76 and a Doppler processor 78. The B mode processor 76 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 78 processes temporally distinct signals from tissue movement and blood flow for the detection of the motion of substances such as the flow of blood cells in the image field. The Doppler processor 78 typically includes a wall filter with parameters which may be set to pass and/or reject echoes returned from selected types of materials in the body.

The structural and motion signals produced by the B mode and Doppler processors are coupled to a scan converter 82 and a multi-planar reformatter 94. The scan converter 82 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 92 converts the echo signals of a 3D data set into a projected 3D image as viewed from a given reference point as described in U.S. Pat. No. 6,530,885 (Entrekin et al.).

The 2D or 3D images are coupled from the scan converter 82, multi-planar reformatter 94, and volume renderer 92 to an image processor 80 for further enhancement, buffering and temporary storage for display on an image display 90. In addition to being used for imaging, the blood flow values produced by the Doppler processor 78 and tissue structure information produced by the B mode processor 76 are coupled to a quantification processor 84. The quantification processor produces measures of different flow conditions such as the volume rate of blood flow as well as structural measurements such as the sizes of organs and gestational age. The quantification processor may receive input from the user control panel 88, such as the point in the anatomy of an image where a measurement is to be made. Output data from the quantification processor is coupled to a graphics processor 86 for the reproduction of measurement graphics and values with the image on the display 90, and for audio output from the display device 90. The graphics processor 86 can also generate graphic overlays for display with the ultrasound images. These graphic overlays can contain standard identifying information such as patient name, date and time of the image, imaging parameters, and the like. For these purposes the graphics processor receives input from the user interface 88, such as patient name. The user interface is also coupled to the transmit transducer controller 68 to control the generation of ultrasound signals from the transducer array 60' and hence the images produced by the transducer array and the ultrasound system. The transmit control function of the transducer controller 68 is only one of the functions performed. The transducer controller 68 also takes account of the mode of operation (given by the user) and the corresponding required transmitter configuration and bandpass configuration in the receiver analog to digital converter. The transducer controller 68 can be a state machine with fixed states.

The user interface is also coupled to the multi-planar reformatter 94 for selection and control of the planes of multiple multi-planar reformatted (MPR) images which may be used to perform quantified measures in the image field of the MPR images.

Although in the detailed description herein above the construction and operation of devices and systems according to the invention have been described for EAPs, the invention may in fact be used for devices based on other kinds of responsive material, including other kinds of EAM material. Hence, unless indicated otherwise, the EAP materials hereinabove can be replaced with other responsive materials such as other EAM materials. Such other responsive materials are known in the art and the person skilled in the art will know where to find them and how to apply them.

Materials suitable for an EAP element are known. Electro-active polymers include, but are not limited to, the sub-classes: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels and polymer gels.

The sub-class electrostrictive polymers includes, but is not limited to:

Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The sub-class dielectric elastomers includes, but is not limited to: acrylates, polyurethanes, silicones.

The sub-class conjugated polymers includes, but is not limited to: polypyrrole, poly-3,4-ethylenedioxythiophene, poly(p-phenylene sulfide), polyanilines.

In all of these examples, additional passive layers may be provided for influencing the electrical and/or mechanical behavior of the EAP element in response to an applied electric field.

Each EAP element may be sandwiched between electrodes. The electrodes may be stretchable so that they follow the deformation of the EAP material. Materials suitable for the electrodes should be ultrasound-transmissive and include for instance thin metal films, such as gold, copper, or aluminum or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT:PSS).

If the electrodes are arranged in a non-symmetric configuration, the imposed voltage can induce all kinds of deformations such as twisting, rolling, torsioning, turning, and non-symmetric bending deformation.

As discussed above, embodiments of the invention make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An ultrasound interface element, comprising:
    an ultrasound-transmissive active layer comprising one or more responsive material elements comprising an electroactive material (EAM) and adapted to deform in response to an electromagnetic stimulus, and the ultrasound-transmissive active layer having an upper contact surface adapted for application to an incident tissue surface, the ultrasound-transmissive active layer being configurable in a first state in which an initial line or area portion of the upper contact surface of the ultrasound-transmissive active layer is raised relative to a surrounding area portion; and
    a controller adapted to control the one or more responsive material elements to deform out-of-plane of the ultrasound-transmissive active layer such as to cause the initial line or area portion to expand smoothly outwards to form a final, larger area portion to thereby establish between the ultrasound-transmissive active layer and the incident tissue surface a progressively expanding interface, wherein the control comprises either controlling an array of responsive material elements comprised by the ultrasound-transmissive active layer to deform in a first sequential pattern outward from the initial line or area portion and across the larger area portion.

2. The ultrasound interface element as claimed in claim 1, wherein the ultrasound-transmissive active layer comprises a responsive material element which extends across the entire ultrasound-transmissive active layer and the controller is adapted to control the responsive material element to progressively move from an initial convex shape to a less convex shape, such that when applied to the incident tissue surface, a conforming interface is established, expanding progressively outward from an apex of the initial convex shape to a broader region of the less convex shape.

3. The ultrasound interface element as claimed in claim 1, wherein:
    the controller is adapted to control the elements of the array of responsive material elements to deform in a second sequential pattern outwardly from a single element or line of elements within the array of responsive material elements, corresponding to the initial line or area portion, such as to establish the progressively expanding conforming interface between the ultrasound-transmissive active layer and the incident tissue surface, an area of the interface expanding outward from the single element or a line as the responsive material elements are controlled.

4. The ultrasound interface element as claimed in claim 3, wherein:
    the controller is adapted to control the responsive material elements to deform in a third sequential pattern outwardly in all directions from the single element or line; or
    the controller is adapted to control the elements to deform in a fourth sequential pattern outwardly in a subset of one or more directions from the single element or line.

5. The ultrasound interface element as claimed in claim 3, wherein the ultrasound interface element comprises a deformable ultrasound-transmissive active layer adapted to sense a pressure distribution between the ultrasound-transmissive active layer and the tissue surface.

6. The ultrasound interface element as claimed in claim 5, wherein the controller is adapted to:
    identify, based on the sensed distribution, a line or sub-region of lowest contact pressure between the ultrasound-transmissive active layer and the tissue surface;
    identify a single responsive material element or line of elements spatially aligned with the identified sub-region or line; and
    select the identified single element or line of elements as the single element or line of elements of the fourth sequential pattern.

7. The ultrasound interface element as claimed in claim 5, wherein the ultrasound-transmissive active layer adapted to sense the pressure distribution between the ultrasound-transmissive active layer and the tissue surface is provided by one or more of the responsive material elements, the controller being adapted to sense contact pressure based on pressure-induced electrical outputs generated by the one or more elements upon an initial manual application of the ultrasound-transmissive active layer to the tissue surface.

8. The ultrasound interface element as claimed in claim 1, wherein the ultrasound interface element comprises a vibrator adapted to induce vibrations in the ultrasound-transmissive active layer, and the vibrator is provided by one or more of the responsive material elements, the controller being adapted to control the elements to exhibit oscillatory deformation.

9. The ultrasound interface element as claimed in claim 1, wherein the ultrasound interface element comprises an electrode array disposed on the ultrasound-transmissive active layer, and the controller is adapted to identify regions of contact between the ultrasound-transmissive active layer and the tissue surface.

10. The ultrasound interface element as claimed in claim 9, wherein electrodes of the electrode array disposed on the ultrasound-transmissive layer are individually addressable, and distributed across a major surface of the ultrasound-transmissive active layer and electrically coupled to the controller, and optionally wherein the controller is adapted to:
    detect current flow between any two of the electrodes and use the current flow as indication of contact between the electrodes and the tissue surface; or
    monitor capacitance between one or more pairs of the electrodes and use changes in the capacitance as indication of contact between the electrodes and the tissue surface.

11. The ultrasound interface element as claimed in claim 10, wherein the electrode of the electrode array is used both for stimulating deformation of the responsive material elements and for sensing contact between the ultrasound-transmissive active layer and the tissue surface.

12. The ultrasound interface element as claimed in claim 1, wherein the controller is adapted in accordance with one control mode to control one or more of the responsive material elements to deform in directions substantially parallel with a surface of the ultrasound-transmissive active layer such as to encourage lateral transport of an interfacing fluid or gel disposed between the ultrasound-transmissive active layer and the tissue surface.

13. An ultrasound device, comprising:
a carrier;
one or more ultrasound transducers distributed on the carrier; and
an ultrasound interface element as claimed in claim 1 arranged in an acoustic output path of the one or more ultrasound transducers, for facilitating interface between the ultrasound transducers and an incident tissue surface to which the ultrasound device is adapted to be applied.

14. The ultrasound interface element as claimed in claim 1, wherein the EAM comprises an electroactive polymer (EAP).

15. A method of establishing interface between an ultrasound interface element and an incident tissue surface to which the ultrasound interface element is adapted to be applied, the ultrasound interface element comprising an ultrasound-transmissive active layer, the ultrasound-transmissive active layer comprising one or more responsive material elements comprising an electroactive material (EAM) and adapted to deform in response to an electromagnetic stimulus, and
wherein the ultrasound-transmissive active layer is configurable in a first state in which an initial line or area portion of an upper contact surface of the ultrasound-transmissive active layer is raised relative to a surrounding area portion;
and the method comprising:
controlling the one or more elements to deform out-of-plane of the ultrasound-transmissive active layer such as to cause the initial line or area portion to expand smoothly outwards to form a final, larger area portion to thereby progressively establish an interface between the ultrasound-transmissive active layer and an incident tissue surface,
the control comprising either controlling an array of responsive material elements comprised by the ultrasound-transmissive active layer to deform in a first sequential pattern outward from the initial line or area portion and across the larger area portion.

16. An ultrasound interface element, comprising:
an ultrasound-transmissive active layer comprising one or more responsive material elements adapted to deform in response to an electromagnetic stimulus, and the ultrasound-transmissive active layer having an upper contact surface adapted for application to an incident tissue surface, the ultrasound-transmissive active layer being configurable in a first state in which an initial line or area portion of the upper contact surface of the ultrasound-transmissive active layer is raised relative to a surrounding area portion; and
a controller is adapted to control the one or more responsive material elements to deform out-of-plane of the ultrasound-transmissive active layer such as to cause the initial line or area portion to expand smoothly outwards to form a final, larger area portion to thereby establish between the ultrasound-transmissive active layer and the incident tissue surface a progressively expanding interface, wherein the control comprises either controlling an array of responsive material elements comprised by the ultrasound-transmissive active layer to deform in a first sequential pattern outward from the initial line or area portion and across the larger area portion.

17. The ultrasound interface element as claimed in claim 16, wherein:
the ultrasound-transmissive active layer comprises an array of responsive material elements, and
the controller is adapted to control the elements of the array of responsive material elements to deform in a second sequential pattern outwardly from a single element or line of elements within the array, corresponding to the initial line or area portion, such as to establish the progressively expanding conforming interface between the ultrasound-transmissive active layer and the incident tissue surface, an area of the interface expanding outward from the single element or line as the responsive material elements are controlled.

18. The ultrasound interface element as claimed in claim 17, wherein the ultrasound interface element comprises a deformable active layer adapted to sense a pressure distribution between the ultrasound-transmissive active layer and the tissue surface.

19. The ultrasound interface element as claimed in claim 18, wherein the controller is adapted to:
identify, based on the sensed distribution, a line or sub-region of lowest contact pressure between the ultrasound-transmissive active layer and the tissue surface;
identify a single responsive material element or line of elements spatially aligned with the identified sub-region or line; and
select the identified single element or line of elements as the single element or line of elements of the first sequential pattern.

20. The ultrasound interface element as claimed in claim 16, wherein the ultrasound interface element comprises means for inducing vibration of the ultrasound-transmissive active layer, and the means for inducing vibration is provided by one or more of the responsive material elements, the controller being adapted to control the elements to exhibit oscillatory deformation.

* * * * *